United States Patent [19]
Akiyama et al.

[11] Patent Number: 5,693,945
[45] Date of Patent: Dec. 2, 1997

[54] GAS ANALYZER

[75] Inventors: Shigeyuki Akiyama; Masahiko Fujiwara; Fujio Koga; Naohito Shimizu; Toshihiko Uno; Aritoshi Yoneda, all of Miyanohigashi-machi, Japan

[73] Assignee: Horiba Ltd., Kyoto, Japan

[21] Appl. No.: 508,816

[22] Filed: Jul. 28, 1995

[30] Foreign Application Priority Data

Jul. 30, 1994 [JP] Japan ................................. 6-197610
Oct. 22, 1994 [JP] Japan ................................. 6-282935

[51] Int. Cl.$^6$ ................................................. G01N 21/61
[52] U.S. Cl. .................... 250/345; 250/339.13; 250/343; 250/373
[58] Field of Search ......................... 250/373, 343, 250/339.13, 345

[56] References Cited

U.S. PATENT DOCUMENTS

| | | | |
|---|---|---|---|
| 3,571,589 | 3/1971 | Barringer | 250/373 |
| 3,860,344 | 1/1975 | Garfunkel | 250/339.13 |
| 3,869,613 | 3/1975 | Link et al. | 250/343 |
| 3,970,430 | 7/1976 | Reader, Jr. et al. | 250/373 |
| 4,297,577 | 10/1981 | Coe et al. | 250/343 |
| 4,914,719 | 4/1990 | Conlon et al. | 250/343 |
| 5,572,032 | 11/1996 | Fujiwara et al. | 250/345 |

*Primary Examiner*—Carolyn E. Fields
*Attorney, Agent, or Firm*—Oppenheimer Poms Smith

[57] ABSTRACT

An ultraviolet light source is provided on one end of a cell into which a sample gas is introduced. A beam splitter for dividing beams which have been transmitted through the cell into two optical paths is provided on the other end of the cell. A first detector is provided in one optical path, and a second detector is provided in the other optical path. A gas filter filled with a component to be measured is positioned between the detectors and beam splitter so that a concentration of the component to be measured may be obtained on the basis of a difference between the output of the first detector and the product of the output of the second detector and an appointed constant. Influences resulting from components coexisting in the sample gas are reduced. Alternatively, an infrared light source may be provided on one end of a sample cell. A gas filter filled with a gas the same as the gas to be measured is provided at the other end of the sample cell. A reference filter filled with a non-absorbing gas is positioned parallel to the gas filter. A beam splitter and a detector are sequentially disposed downstream from the gas filter, and a mirror is disposed downstream from the reference filter. The mirror is positioned such that beams which passed through the reference filter may be directed to the beam splitter and, subsequently, the detector.

10 Claims, 3 Drawing Sheets

GAS ANALYZER

BACKGROUND OF THE INVENTION

1. Field of the Invention

The present invention relates to gas analyzers such as ultraviolet gas analyzers using non-dispersive ultraviolet absorptiometry (NDUV) in which ultraviolet rays from an ultraviolet light source are transmitted through a cell supplied with a sample gas and are detected by a detector, and such as infrared gas analyzers using non-dispersive infrared absorptiometry (NDIR) in which infrared rays from an infrared light source are transmitted through a cell supplied with a sample gas and are detected by a detector.

2. Description of Related Art

Ultraviolet gas analyzers using NDUV methods have been used for measuring concentrations of $SO_2$ contained in, for example, a combustion exhaust gas. In order to reduce as far as possible interferential influences by $CO_2$ and water, which are interferential components coexisting in a sample gas, a construction as shown in FIG. 10 has been adopted. Reference numeral 1 designates, for example, a cylindrical cell sealed by means of cell windows 2, 3 superior in ultraviolet transmittance at both ends thereof and provided with an inlet port 4 and an outlet port 5 for a sample gas or a reference gas.

An ultraviolet light source 6 is provided at one end of the cell 1, the ultraviolet light source 6 being, for example, a low-pressure mercury lamp. A slit 7 serves as a stop disposed between the cell 1 and the ultraviolet light source 6. A detector 8 is provided at the other end of the cell 1, the detector 8 being, for example, a silicon photodiode. An interference filter 9, for example, a band pass filter, is disposed between the cell 1 and the detector 8 for transmitting ultraviolet rays having a specified wavelength through the cell 1.

A gas change-over supply device 10 alternately supplies the cell 1 with a sample gas S and a reference gas R. The gas change-over supply device 10 is in the form of, for example, a rotary valve. The supply device 10 is provided with two gas inlet ports 11, 12 and two gas outlet ports 13, 14, as well as a rotor 15 as a change-over member. A sample gas line 17 having a semipermeable diaphragm dehumidifier 16 and a reference gas line 18 are connected with the gas inlet ports 11, 12, respectively. The gas outlet port 13 is connected with the gas inlet port 4 of the cell 1, and the gas outlet port 14 is connected with an exhaust portion (not shown).

In an ultraviolet gas analyzer having the above-described construction, ultraviolet rays having a wavelength of 280 nm are emitted from the ultraviolet light source 6. The rotor 15 is rotated at an appointed speed in the direction shown by an arrow in FIG. 10 by means of a motor (not shown) under the condition that the ultraviolet rays are incident upon the cell 1 to alternately supply the sample gas S and the reference gas R, whereby an output expressing the concentration of $SO_2$ from the detector 8 is obtained.

However, the following disadvantages have occurred in ultraviolet gas analyzers having the above-described construction shown in FIG. 10. The interference filter 9 has high selectivities for components to be measured, but, consequently, an interferential influence by $CO_2$ and water cannot be greatly reduced; thus, a considerable interferential influence has been given. In addition, water contained in the sample gas S can be removed by providing the sample gas line 17 with the semipermeable diaphragm dehumidifier 16; however, the semipermeable diaphragm dehumidifier 16 is not only considerably expensive, but the semipermeable diaphragm dehumidifier 16 also consumes a large quantity of dry air for use in purging, thereby increasing costs.

Additionally, infrared gas analyzers using an infrared light source have been known as gas analyzers having the same construction as the above-described ultraviolet gas analyzer. In such an infrared gas analyzer, in general one component is detected using one optical path, and, in the case where a plurality of components are simultaneously measured, two components are detected using two optical paths, even in single cell mode; thus, a large number of parts are required in such an optical system. In addition, in the case where three or four components are simultaneously measured, not only is it required to prepare two gas analyzer units, even in a cross-modulation single cell mode (in which a sample gas and a reference gas are alternately introduced into two measuring cells through a device similar to the gas change-over supply device 10 shown in FIG. 10), but it is also required to prepare two systems of sample gas flow rate from a sampling device. Consequently, not only are the number of parts in such an optical system increased, thereby complicating the sampling system and increasing the cost of plant and equipment, but the maintenance of a plurality of analyzers is also required, thereby increasing the running cost.

SUMMARY OF THE INVENTION

The present invention has been achieved in view of the above-described matters, and it is a primary object of the present invention to provide an ultraviolet gas analyzer capable of surely and inexpensively reducing influences by components coexisting in a sample gas. It is another object of the present invention to provide an infrared gas analyzer capable of simultaneously detecting two or more components in a single-cell mode and judging whether or not a gas to be measured is introduced into one sample cell.

In order to achieve the above-described objects, an ultraviolet light source is provided on one end of a cell, into which cell a sample gas is introduced. A beam splitter for dividing beams which have been transmitted through the cell into two optical paths is provided on the other end of the cell. A first detector is provided in one optical path, and a second detector is provided in the other optical path. A gas filter filled with a component to be measured is positioned between the detectors and the beam splitter so that a concentration of the component to be measured may be obtained on the basis of a difference between an output of the first detector and a product of an output of the second detector and an appointed constant.

In order to achieve the objects of the invention, an ultraviolet light source is provided on one end of a cell into which a sample gas is introduced. An interference filter is provided on the other end of the cell. A first detector is provided in an optical path on the transmission side of the interference filter, and a second detector is provided in an optical path on the reflection side of the interference filter. A gas filter filled with a component to be measured is positioned between the second detector and the interference filter. A concentration of the component to be measured may be obtained from a difference between the output of the first detector and a product of the output of the second detector and an appointed constant.

According to one aspect of the invention, outputs resulting from coexisting components can be brought to zero or a value close to zero by a differential calculation of the outputs from the two detectors; thus, interferential influences can be greatly reduced. Moreover, as it is not required to provide an expensive semipermeable diaphragm dehumidifier, the apparatus can be made inexpensively as a whole, and the operating costs can be remarkably reduced.

Furthermore, according to another aspect of the invention, an infrared light source is provided on one end of a cell into which a sample gas is introduced. A beam splitter is provided on the other end of the cell; a measuring detector is provided in one optical path of the beam splitter; and a gas filter filled with the same gas as a gas to be measured and a reference detector are provided in another optical path of the beam splitter.

According to still another aspect of the invention, as the beam splitter is provided on the other end of the cell, the gas filter, the reference detector, and the measuring detector can be arranged either on the transmission side or on the reflection side of the beam splitter; thus, the respective signal quantities of the measuring detector and the reference detector can be simultaneously detected by single-cell mode. As the gas filter is filled with the same gas as the gas to be measured, the signal quantities are changed in ratio or difference in the case where a gas the same as the gas filled in the gas filter is introduced into the cell and in the case where a gas different from the gas filled in the gas filter is introduced into the cell. Accordingly, it can be determined whether or not the gas introduced into the cell is the gas to be measured by the ratio or difference in signal quantity. Moreover, a concentration of the gas to be measured can be measured by a concentration operation of the signal from the measuring detector after this determination.

Another aspect of the invention is that an infrared light source is provided on one end of a cell into which a sample gas is introduced, and a plurality of beam splitters are provided on the other end of the cell so as to be optically in series with the cell. A measuring detector is provided in one optical path of a last beam splitter, and a gas filter filled with a gas to be measured and a reference detector are provided in another optical path of the last beam splitter. Gas filters filled with the gas to be measured and corresponding reference detectors are provided in optical paths at a right-angle direction with the direction in which the beam splitters are arranged.

The plurality of beam splitters are provided on one end of the cell so as to be optically in series with the cell; therefore, the gas filters and the reference detectors and the measuring detectors can be arranged either on the transmission side or on the reflection side of the beam splitters; thus, the respective signal quantities of the measuring detectors and the reference detectors can be simultaneously detected by a single-cell mode.

According to a further aspect of the invention, a plurality of gas filters and a plurality of reference detectors are provided. The signal quantities of the reference detectors can be obtained separately and in real time. As a result, by using the signal quantities from the respective reference detectors, not only are two or more gases to be measured able to be simultaneously detected by a single-cell mode, but influences by interferential gas components hindering detections of the respective gases to be measured can be compensated.

Yet another aspect of the invention is that an infrared light source is provided on one end of a cell in which a sample gas is introduced. A gas filter filled with a gas the same as a gas to be measured and a reference filter filled with a gas showing no infrared absorption relating to a measurement are provided optically in parallel with each other on the other end of the cell. A beam splitter and a detector are provided optically in series with each other on the downstream side of the gas filter. A mirror is provided on the downstream side of the reference filter. The mirror is switchable between optical paths so that beams which have been transmitted through the reference filter may be guided to the detector by the mirror and the beam splitter when the mirror is switched in the optical path.

According to another aspect of the invention, the beams which have been transmitted through the reference filter can be guided to the detector by the mirror and the beam splitter when the mirror is switched in the optical path, so that a signal quantity incident on the detector can be obtained as a total of a signal quantity due to the beams which have been transmitted through the reference filter and through the gas filter. The signal quantity due to the beams which have been transmitted through only the gas filter is obtained when it is switched out of the optical path. Consequently, it can be determined from a ratio or a difference between the signal quantity obtained when the mirror is switched in the optical path and when the mirror is switched out of the optical path whether or not a gas introduced into the cell is a gas to be measured. Moreover, a concentration of the gas to be measured can be measured by a concentration operation of the signal from the detector after this determination.

A solid detector according to another aspect of the invention is both a measuring detector and a reference detector, so that a difference due to detector characteristics is reduced when compared to the case where the measuring detector and the reference detector are separately used.

The various novel features of the invention which are believed to achieve these goals as well as to provide other advantages and improvements will be understood from the following specification and accompanying drawings in which preferred embodiments of the invention are illustrated by way of example. It is expressly understood, however, that the specification and drawings are for purposes of description and illustration only and are not intended as a definition of the limits of the invention as set forth in the claims.

DETAILED DESCRIPTION OF THE PREFERRED EMBODIMENTS

Figure 1:
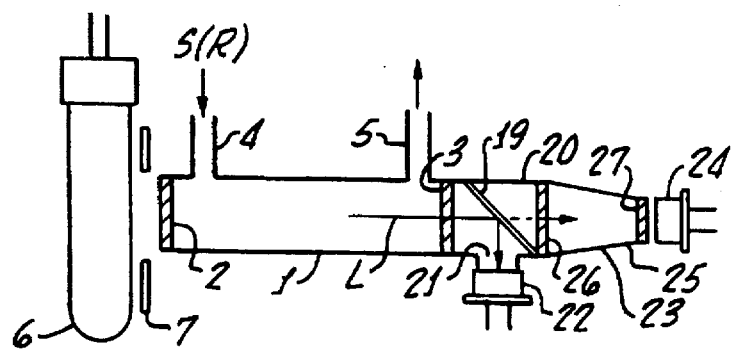
FIG. 1 is a schematic diagram showing a preferred embodiment of the present invention.

FIG. 1 shows a preferred embodiment of the present invention. A construction of an ultraviolet gas analyzer for measuring, for example, $SO_2$ is generally shown. Referring to FIG. 1, reference numeral 1 designates, for example, a cylindrical cell sealed by means of cell windows 2 and 3 superior in ultraviolet transmittance at both ends thereof and provided with an inlet port 4 and an outlet port 5 for a sample gas or a reference gas. An ultraviolet light source 6 is provided at one end of the cell 1, the ultraviolet light source 6 being, for example, a low-pressure mercury lamp. A slit 7 serves as a stop disposed between the cell 1 and the ultraviolet light source 6. Reference numeral 19 designates a beam splitter formed of, for example, a half mirror provided outside the cell window 3 of the cell 1 and housed in a suitable case 20 so as to be inclined at an angle of 45° relative to a horizontal optical axis L. An opening 21 of suitable size is formed in an optical path (shown by a full line in FIG. 1) on the side of the beam-reflecting direction (below the case 20 in FIG. 1) in the beam splitter 19 within the case 20, and a first detector 22 is provided so as to face the opening 21. In addition, a second detector 24 is provided in an optical path (shown by a dashed line in FIG. 1) on the side of the beam-transmitting direction (on the right side of the case 20 in FIG. 1) in the beam splitter 19 within the case 20 through a gas filter 23.

The first detector 22 and the second detector 24 are formed of, for example, a silicon diode. In addition, a case 25 defining the gas filter 23 is sealed by windows 26 and 27, which are superior in ultraviolet transmittance, at both ends thereof. The gas filter 23 is filled with the same gas as a gas to be detected, that is, $SO_2$ in the present preferred embodiment. A side surface of the case 25 defining the gas filter 23 is tapered from the side of the first window 26 to the side of the second window 27. Thus, an opening on the side of a light source can be set into an opening on the side of the detectors.

In operation, ultraviolet rays which have been transmitted through the cell 1 are divided by the beam splitter 19 so that a beam quantity in the optical path on the side of the beam-reflecting direction and in the optical path on the side of the beam-transmitting direction may amount to one-half, respectively. Ultraviolet rays which have arrived at the optical path on the side of the beam-reflecting direction are incident upon the first detector 22, so that a signal of $SO_2$, which is a component to be measured, is increasingly detected while signals of coexisting components are decreasingly detected. In addition, ultraviolet rays which have arrived at the optical path on the side of the beam-transmitting direction are absorbed by $SO_2$ when they pass through the gas filter 23, so that the signal of $SO_2$ is detected at a dramatically reduced level and the signals of the coexisting components are detected at a reduced level in the second detector 24.

Outputs of both detectors 22 and 24 are operated as follows in a signal-operating portion (not shown) to obtain a concentration C of $SO_2$ which is the component to be measured. Provided that the outputs of the detectors 22 and 24 are a and b, respectively, the following expression (1) holds true:

$$C \propto a - \alpha b \quad (\text{wherein } 0 < \alpha \leq 10) \qquad (1)$$

In addition, in the case where the output b of the second detector 24 does not give a linear signal for concentrations of the coexisting components, it is preferable to use a linearization circuit.

With the ultraviolet gas analyzer having the above-described constructions, the output due to the coexisting components can be reduced to zero or a value close to zero by merely performing a differential calculation on the outputs of the first detector 22 and the second detector 24, and, thus, the concentration of the component to be measured can be accurately obtained without being influenced by the coexisting components. In addition, it is not required to provide an expensive semipermeable diaphragm dehumidifier, so that not only can the apparatus be made inexpensively on the whole, but the running cost can also be remarkably reduced.

Although it is desirable for the signals of both detectors 22 and 24 for the coexisting components to be almost the same level, beam quantities to both detectors 22 and 24 can be adjusted also by means of the beam splitter 19 in an optical system. Thus, for example, any fluctuation of the ultraviolet light source 6 can be compensated.

Figure 2:
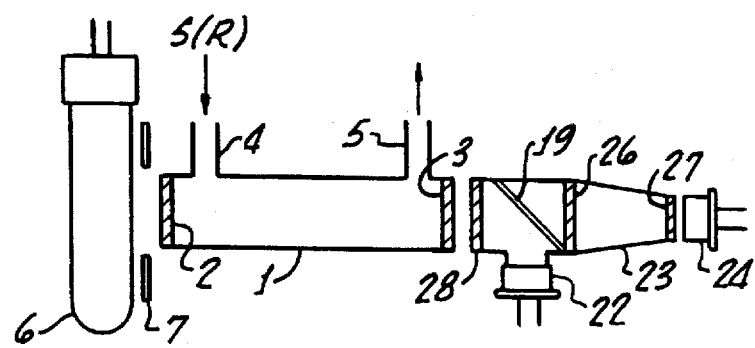
FIG. 2 is a diagram showing another preferred embodiment of the invention.

FIG. 2 shows another exemplary embodiment of the invention. According to this preferred embodiment, which employs an ultraviolet gas analyzer according to the above-described embodiment, an interference filter 28 formed of, for example, a band-pass filter is disposed between the cell 1 and the beam splitter 19. With this construction, a signal-to-noise (S/N) ratio in the first detector 22 can be improved, and the accuracy of measurement can be increased as a result.

In addition, although the first detector 22 is provided in the optical path on the side of the beam-reflecting direction of the beam splitter 19, and the gas filter 23 and the second detector 24 are provided in the optical path on the side of the beam-transmitting direction of the beam splitter 19 in the above-described preferred embodiments, the first detector 22 may be provided in the optical path on the side of the beam-transmitting direction of the beam splitter 19, and the gas filter 23 and the second detector 24 may be provided in the optical path on the side of the beam-reflecting direction of the beam splitter 19.

Figure 3:
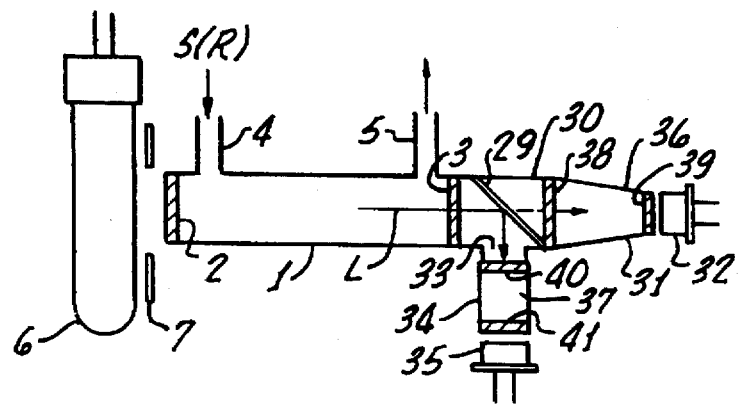
FIG. 3 is a diagram showing a further preferred embodiment of the invention.

Moreover, although the component to be measured and the coexisting components are detected in the same wavelength band to differentially operate the detected outputs in the above-described preferred embodiments, the present invention is not limited by this in that the further exemplary embodiment shown in FIG. 3 may be adopted. Referring to FIG. 3, reference numeral 29 designates an interference filter formed of, for example, a band-pass filter provided outside the cell window 3 of the cell 1 and housed in the suitable case 30 so as to be inclined at an angle of 45° relative to a horizontal optical axis L. The interference filter 29 is adapted to transmit ultraviolet rays within an appointed wavelength band including an absorption peak wavelength (280 nm) of $SO_2$, which is the component to be measured. The interference filter 29 is also adapted to reflect ultraviolet rays outside the appointed wavelength band.

A first detector 32 is provided in an optical path (shown by a dashed line in FIG. 3) on the side of the beam-transmitting direction (on the right side of case 30 in FIG. 3) of the interference filter 29 within the case 30 through a gas filter 31. In addition, an opening 33 of suitable size is formed in an optical path (shown by a solid line in FIG. 3) on the side of the beam-reflecting direction (below the case 30 in FIG. 3) of the interference filter 29 with the case 30. A gas filter 34 is provided to face the opening 33. In addition, a second detector 35 is provided on the downstream side of the gas filter 34.

The first detector 32 and the second detector 35 are formed of, for example, a silicon diode. In addition, a case 36 defining the gas filter 31 is sealed by windows 38 and 39, and a case 37 defining the gas filter 34 is sealed by windows 40 and 41. The windows 38 to 41 are superior in ultraviolet transmittance at both end portions thereof. The case 36 defining the gas filter 31 is filled with $CO_2$, which is an interference component when the component to be measured is $SO_2$. A side surface of the case 36 defining the gas filter 31 is tapered from the side of the window 38 to the side of the window 39. Thus, an opening on the side of a light source can be set into an opening on the side of the detectors.

In an ultraviolet gas analyzer having the above-described construction, the first detector 32 detects mainly the concentration of the component to be measured within the absorption wavelength band of the component to be measured, while the second detector 35 detects the concentrations of coexisting components within a wavelength band on the outskirts of the absorption wavelength band of the component to be measured.

More specifically, ultraviolet rays which have been transmitted through the cell 1 within the absorption wavelength band of $SO_2$ pass through the interference filter 29 to be incident upon the first detector 32 through the gas filter 31. These rays are absorbed by $CO_2$ when they are passing through the gas filter 31, so that a signal of $SO_2$, which is the component to be measured, is increasingly detected by the first detector 32 while signals of the coexisting components are decreasingly detected by the first detector 32. In addition, ultraviolet rays which have been transmitted through cell 1 outside the absorption wavelength band of $SO_2$ are reflected by the interference filter 29 to be absorbed by $SO_2$ when they are passing through the gas filter 34, so that the signal of $SO_2$ is detected at a very reduced level by the second detector 35, while the signals of the coexisting components are decreasingly detected. Consequently, the concentration of the component to be measured ($SO_2$) can be obtained on the basis of expression (1) provided above. It is noted that the gas filter 31 may be omitted in this preferred embodiment.

The embodiments of the present invention described above can be similarly applied not only to the above-described ultraviolet gas analyzer for use in measuring the concentration of $SO_2$ but also to the ultraviolet gas analyzers measuring other gases, for example, ammonia gas, chlorine gas, mercury vapor, nitrogen monoxide, hydrogen sulfide, and the like.

As described above, according to these embodiments of the invention, the ultraviolet rays which have passed through the cell are divided into two optical paths, each optical path being provide with a detector therein. The outputs from these two detectors are differentially calculated, so that the output due to the coexisting components can be reduced to zero or a value close to zero; thus, the interferential influences can be surely reduced. In addition, it is not required to provide an expensive semipermeable diaphragm dehumidifier, so that not only can the apparatus be made inexpensively on the whole but the running costs can also be remarkable reduced. Moreover, the above-described embodiments are particularly effective in the case where the detector has no selectivity for the component to be measured.

Further exemplary embodiments of the present invention will be described below with reference to FIGS. 4 to 9. These embodiments relate to infrared gas analyzers.

Figure 4:
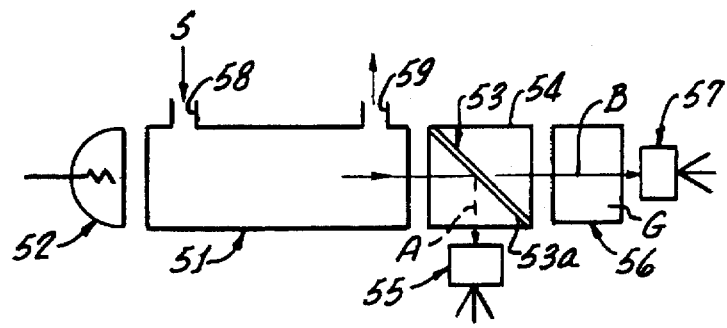
FIG. 4 is a diagram showing still another preferred embodiment of the invention.

FIG. 4 shows a preferred embodiment of the invention. An infrared gas analyzer according to this preferred embodiment is a single cell-type analyzer in which a measuring solid detector and a reference solid detector are used. A gas filter filled with a gas to be measured is provided on the upstream side of the reference detector. Such analyzer not only determines whether a gas which is being introduced into a cell is a gas to be measured, but it also measures a concentration of the gas to be measured by comparing outputs from these two detectors.

More specifically, reference numeral 51 designates a cell into which a sample gas S is introduced. The cell 51 is provided with an infrared light source 52 on one end thereof and a chamber 54 including a half mirror 53 as a beam splitter on the other end thereof. A measuring detector 55 formed of, for example, a solid detector is provided on the optical path-A side of the half mirror 53, and a gas filter 56 is filled with gas G, which is the same as the gas to be measured, and a reference detector 57 formed of, for example, a solid detector are provided on the optical path-B side of the half mirror 53. In addition, reference numeral 58 designates an inlet port for sample gas S provided in the cell 51, and reference numeral 59 designates an outlet port for the sample gas S provided in cell 51.

The half mirror 53 is provided within the chamber 54 so that a transmitting and reflecting surface 53a thereof may be inclined at an angle of 45° relative to optical paths A and B, respectively.

In addition, although the quantity of light incident on the measuring detector 55 and the reference detector 57 is in general divided therebetween at a 1:1 ratio by means of the half mirror 53, in the case where the half mirror 53 exhibits a difference of sensitivity proper to the solid detectors, a reflection factor of the half mirror 53 is adjusted to 1:2 or more to distribute the light quantities corresponding to detecting sensitivities of both detectors 55 and 57.

As the infrared gas analyzer according to this preferred embodiment has the above-described construction, the sample gas S is sent in the cell 51, and a change in light quantity due to the component to be measured (i.e, the gas to be measured) absorbed in the cell 51 is equally divided between the measured detector 55 and the reference detector 57 by the half mirror 53. Signals from the respective detectors 55 and 57 are amplified and outputted.

The gas filter 56 is filled with the same gas G as the component to be measured. Consequently, the signal quantities are changed in ratio or difference in the case (1) where a gas the same as the gas filled in the gas filter 56 is introduced into the cell 51 and (2) where a gas different from the gas filled in the gas filter 56 is introduced into the cell 51; therefore, it can be determined whether the gas introduced into the cell 51 is the gas to be measured or not by the ratio or difference in signal quantity. Moreover, a concentration of the gas to be measured can be measured by a concentration operation of the signal from the measuring detector 55 after this determination.

Alternatively, the measuring detector 55 may be arranged on the side of the transmitting position on the half mirror 53, and the gas filter 56 and the reference detector 57 may be arranged on the side of the reflecting position of the half mirror 53.

Figure 5:
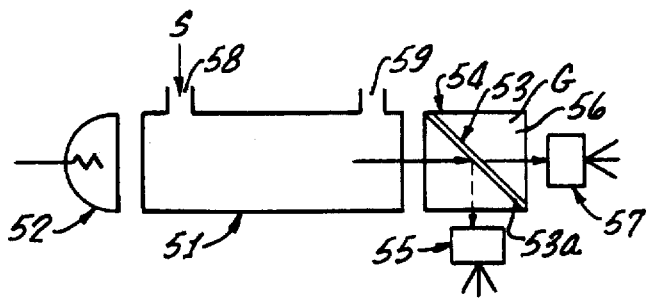
FIG. 5 is a diagram showing yet another preferred embodiment of the invention.

FIG. 5 shows another preferred embodiment of the invention. An infrared gas analyzer according to this preferred embodiment is a single-cell-type analyzer in which a measuring solid detector and a reference solid detector are used. A gas filter filled with a gas to be measured is provided on the upstream side of the reference detector, and a chamber of a half mirror serves as the gas filter.

More specifically, a part of an inside of a chamber 54 of a half mirror 53 is used as a gas filter 56. In addition, a measuring detector 55 may be arranged on the transmitting side of the half mirror 53, and the gas filter 56 and a reference detector 57 may be arranged on the reflecting side of the half mirror 53.

Figure 6:
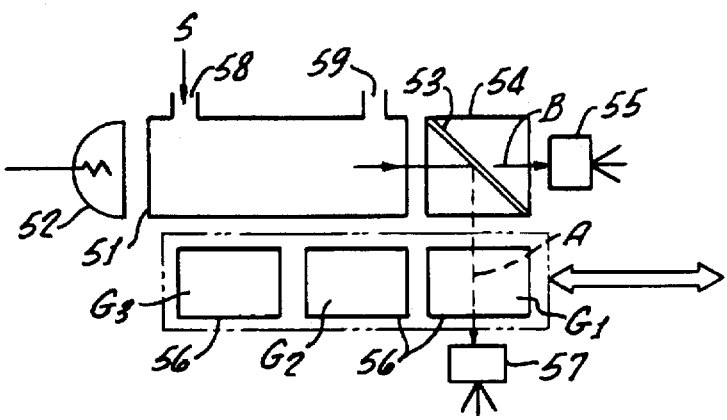
FIG. 6 is a diagram showing still a further preferred embodiment of the invention.

FIG. 6 shows still another preferred embodiment of the invention. The infrared gas analyzer according to this preferred embodiment employs a measuring solid detector, a reference solid detector, and a plurality of gas filters filled with different gases to be measured provided on the upstream side of the reference solid detector. The gas filters are provided so as to be movable in a direction parallel to an optical path.

According to this preferred embodiment, a plurality of gas filters 56 are provided so as to be movable in a direction parallel to an optical path B, so that it is possible to automatically determine whether a plurality of gases to be measured are introduced or not, and to measure their concentrations by filling every gas filter 56 with a gas $G_1$, $G_2$, $G_3$ the same as a gas to be measured and by preparing one reference detector 57 without preparing the reference detectors of a number equal to a number of the gas filters.

Figure 7:
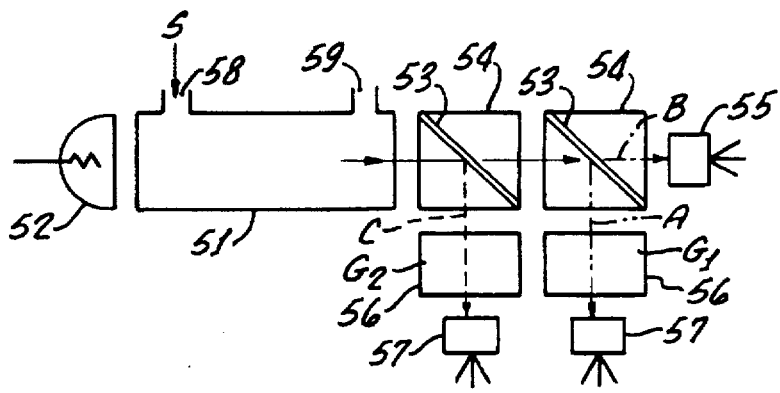
FIG. 7 is a diagram showing yet a further preferred embodiment of the present invention.

FIG. 7 shows still further preferred embodiment of the invention. An infrared gas analyzer according to this preferred embodiment is a single-cell-type analyzer in which one measuring solid detector, a plurality of gas filters, and a plurality of reference detectors are provided, so that two or more gases to be measured can be simultaneously detected, and the influences by interferential gas components hindering detections of the respective gases to be measured can be compensated.

More specifically, an infrared light source 52 is provided on one end of a cell 51, and two half mirrors 53 are provided on the other end of the cell 51 so as to be optically in series with the cell 51. A measuring detector 55 is provided on the optical path-B side of the second half mirror 53. A gas filter 56 filled with the same gas G as the gas to be measured and a reference detector 57 are provided on the optical path-A side of the second half mirror 53. A gas filter 56 filled with the same gas $G_2$ as the gas to be measured and a reference detector 57 are provided on the optical path-C side of the first half mirror 53.

According to this preferred embodiment, a plurality of gas filters 56 and a plurality of reference detectors 57 are provided. Consequently, after an operation to determine whether or not a gas introduced into the cell 51 is the gas to be measured, an operation to measure a concentration of the gas to be measured is started. At this time, two or more gases to be measured can be simultaneously detected. That is to say, in processing a signal from the measuring detector 55, a concentration-operating process is selected in accordance with each gas of a plurality of gases to be measured to measure the concentrations. As a result, two or more gases to be measured can be simultaneously detected in one optical system by initiating this concentration-operating process.

According to this preferred embodiment, there is provided a function capable of compensating the influences of the interferential gas components hindering the detection of the respective gas components to be measured. Specifically, a plurality of gas filters 56 and a plurality of reference detectors 57 are provided, so that signal quantities of the respective reference detectors 57 can be obtained separately and in real time. As a result, by using these signal quantities from the respective reference detectors 57, the compensating operation can be conducted.

Figure 8:
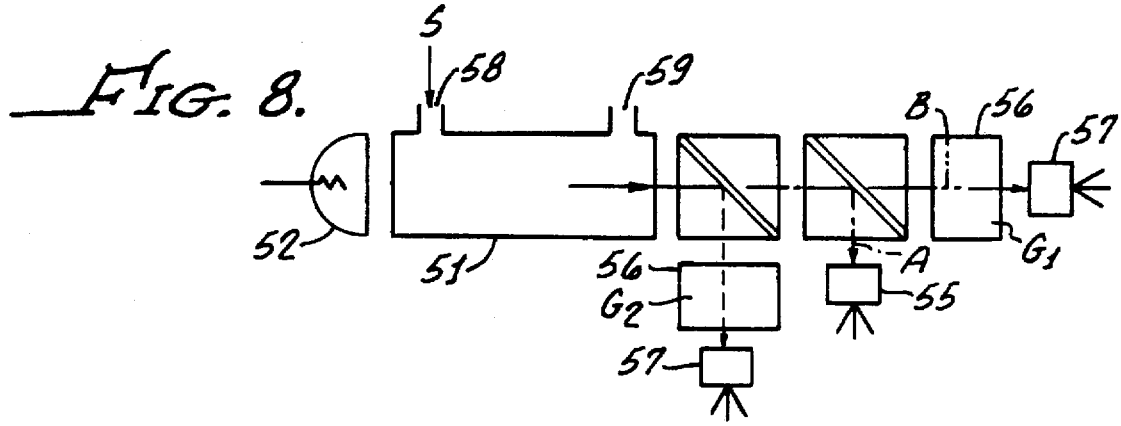
FIG. 8 is a diagram showing yet still another preferred embodiment of the invention.

FIG. 8 shows yet another preferred embodiment of the invention. In a infrared gas analyzer according to this preferred embodiment, the measuring detector 55 and one set of the gas filters 56 and the reference detectors 57 are switched in position from the embodiment shown in FIG. 7. Two or more gases to be measured can be simultaneously detected, and the influences by the interferential gas components hindering the detection of the respective gases to be measured can be compensated in the same manner as described in the preferred embodiment shown in FIG. 7.

Figure 9:
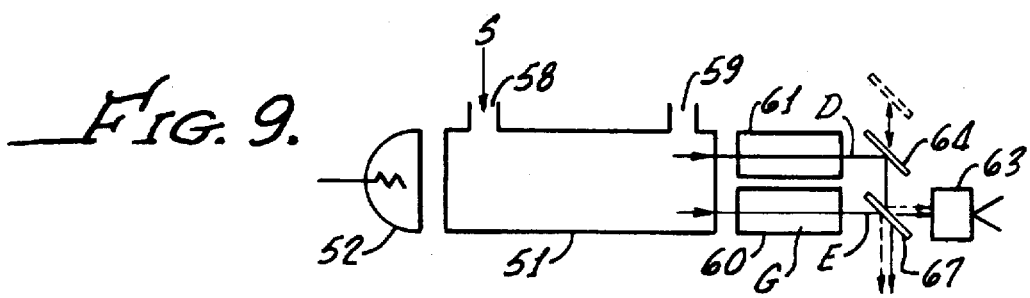
FIG. 9 is a diagram showing yet still a further preferred embodiment of the invention.
Figure 10:
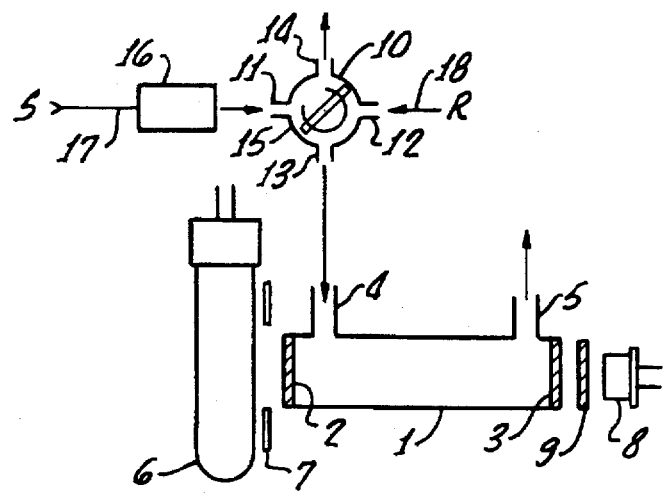
FIG. 10 is a schematic diagram of a gas analyzer according to the prior art.

FIG. 9 shows a further preferred embodiment of the invention. In an infrared gas analyzer according to this preferred embodiment, one solid detector 61 serves as both a measuring detector (see detector 55 of previous figures) and a reference detector (see detector 57 of previous figures). An infrared light source 52 is provided on one end of a cell 51. A gas filter 60 filled with the same gas G as a gas to be measured and a reference filter 61 filled with a gas with no infrared absorption relating to the measurement are provided optically in parallel with each other on the other end of the cell 51. A half mirror 62 and a solid detector 63 are provided optically in series with each other on the downstream side of the gas filter 60, and a mirror 64 is provided on the downstream side of the reference filter 61 in an optical path D. Beams which have been transmitted through the reference filter 61 may be guided to the solid detector 63 by the mirror 64 and the half mirror 62 in that the mirror 64 is switchable in optical path D.

According to this preferred embodiment, the beams which have transmitted through the reference filter 61 may be guided to the solid detector 63 by the mirror 64 and the half mirror 62 when the mirror 64 is switched in optical path D; therefore, a signal quantity incident on the solid detector 63 can be a total of a signal quantity due to the beams which have transmitted through the reference filter 61 and through the gas filter 60. Accordingly, the signal quantity due to the beams which have been transmitted through only the gas filter 60 in optical path E is obtained when the mirror 64 is not in optical path D (as shown in phantom line).

Consequently, it can be determined from a ratio or a difference between the signal quantity obtained when the mirror 64 is switched in optical path D and when the mirror 64 is switched out of optical path D whether or not a gas introduced into the cell 51 is a gas to be measured. Moreover, a concentration of the gas to be measured can be measured by a concentration operation of the signal from the solid detector 63 after this determination. Furthermore, the solid detector 63 serves as both the measuring detector and the reference detector, so that a difference due to detector characteristics is reduced as compared with the case where the measuring detector 55 and the reference detector 57 are separately used. Thus, an advantage is that the signal-to-noise (S/N) ratio is improved.

In addition, the mirror 64 may be a reflecting mirror or a half mirror. Moreover, a pyrosensor, a thermopyrosensor, or a sensor having no selectivity in wavelength, such as a semiconductor sensor, can be employed as the solid detector used in the above-described respective preferred embodiments.

What is claimed is:

1. An ultraviolet gas analyzer comprising:

a cell into which a sample gas is introducible;

an ultraviolet light source provided at one end of said cell for providing beams of ultraviolet light;

a beam splitter provided at the other end of said cell for dividing beams which have transmitted through said cell into a first optical path representing reflected ultraviolet light and a second optical path representing transmitted ultraviolet light;

a first detector disposed in said first optical path, said first detector generating an output responsive to the reflected ultraviolet light incident thereon;

a second detector disposed in said second optical path, said second detector generating an output responsive to the transmitted ultraviolet light incident thereon; and a gas filter filled with a component to be measured disposed between said beam splitter and said second detector.

2. A method for determining a concentration of a component of a sample gas, said method comprising the steps of:
providing the ultraviolet gas analyzer of claim 1;
introducing a sample gas into said cell;
transmitting beams of ultraviolet light; and
calculating the difference between said output of said first detector and the product of said output of said second detector and an appointed constant.

3. An ultraviolet gas analyzer comprising:
a cell into which a sample gas is introducible;
an ultraviolet light source provided at one end of said cell for providing beams of ultraviolet light;
an interference filter provided at the other end of said cell for transmitting and reflecting beams which have transmitted through said cell, said interference filter having a transmission optical path and a reflection optical path;
a first detector provided in said transmission optical path of said interference filter, said first detector generating an output responsive to transmitted ultraviolet light incident thereon;
a second detector provided in said reflection optical path of said interference filter, said second detector generating an output responsive to reflected ultraviolet light incident thereon; and
a gas filter filled with a component to be measured disposed between said interference filter and said second detector.

4. A method for determining a concentration of a component of a sample gas, said method comprising the steps of:
providing the ultraviolet gas analyzer of claim 3;
introducing a sample gas into said cell;
transmitting beams of ultraviolet light; and
calculating the difference between said output of said first detector and the product of said output of said second detector and an appointed constant.

5. An infrared gas analyzer comprising:
a cell into which a sample gas is introducible;
an infrared light source provided at one end of said cell for providing beams of infrared light;
a beam splitter provided at the other end of said cell for dividing beams which have transmitted through said cell into a first optical path representing reflected infrared light and a second optical path representing transmitted infrared light;
a measuring detector disposed in said first optical path;
a reference detector disposed in said second optical path; and
a gas filter filled with a gas the same as a gas to be measured in said sample gas and disposed between said beam splitter and said reference detector.

6. A method for determining a concentration of a component of a sample gas, said method comprising the steps of:
providing the infrared gas analyzer of claim 5;
introducing a sample gas into said cell;
transmitting beams of infrared light; and
calculating the difference between said output of said first detector and said output of said second detector.

7. An infrared gas analyzer comprising:
a cell into which a sample gas is introducible;
an infrared light source provided on one end of said cell for providing beams of infrared light;
a plurality of beam splitters being provided in series at the other end of said cell, each of said plurality of said beam splitters for dividing beams which have transmitted through said cell into a first optical path and a substantially offset second optical path;
a plurality of reference detectors equal to the number of said plurality of said beam splitters, one reference detector of said plurality of reference detectors provided in said second optical path of each beam splitter of said plurality of beam splitters;
a plurality of gas filters equal to the number of said plurality of said beam splitters, each gas filter of said plurality of gas filters filled with a gas to be measured, one gas filter of said plurality of gas filters disposed between each said beam splitter and reference detector; and
a measuring detector provided in said first optical path of the beam splitter of said plurality of beam splitters farthest from said infrared light source.

8. A method for determining a concentration of a component of a sample gas, said method comprising the steps of:
providing the infrared gas analyzer of claim 7;
introducing a sample gas into said cell;
transmitting beams of infrared light; and
calculating the difference between said output of said first detector and said output of said second detector.

9. An infrared gas analyzer comprising:
a cell into which a sample gas is introducible;
an infrared light source provided at one end of said cell for providing beams of infrared light;
a gas filter provided at the other end of said cell, said gas filter filled with a gas the same as a gas to be measured in said sample gas,
a reference filter provided at said other end of said cell parallel to said gas filter, said reference filter filled with a gas having no infrared absorption related to the measurement of said gas to be measured;
a beam splitter disposed downstream of said gas filter;
a detector disposed downstream of and in series with said beam splitter; and
a mirror disposed on the downstream side of said reference filter, said mirror being switchable between:
a position at which beams which have transmitted through said reference filter are reflectable by said mirror to said beam splitter and said detector; and
a position at which beams which have transmitted through said reference filter are not reflectable by said mirror.

10. A method for determining a concentration of a component of a sample gas, said method comprising the steps of:
providing the infrared gas analyzer of claim 9;
introducing a sample gas into said cell;
transmitting beams of infrared light; and
calculating the difference between said output of said first detector and said output of said second detector.

* * * * *